(12) United States Patent
Taylor et al.

(10) Patent No.: US 6,770,437 B1
(45) Date of Patent: Aug. 3, 2004

(54) METHOD FOR ASSIGNING AN INDIVIDUAL TO A POPULATION OF ORIGIN BASED ON MULTI-LOCUS GENOTYPES

(75) Inventors: Jeremy Francis Taylor, Austin, TX (US); Sara L. F. Davis, Bertram, TX (US); Luke Lind, Eaton, CO (US); Scott K. Davis, Bertram, TX (US)

(73) Assignee: ViaGen, Inc., Phoenix, AZ (US)

( * ) Notice: Subject to any disclaimer, the term of this patent is extended or adjusted under 35 U.S.C. 154(b) by 101 days.

(21) Appl. No.: 09/710,340

(22) Filed: Nov. 9, 2000

(51) Int. Cl.$^7$ ............................ C12Q 1/68; C07H 21/04
(52) U.S. Cl. ..................... 435/6; 435/91.1; 435/91.2; 536/23.1; 536/23.5; 536/24.3; 536/24.33
(58) Field of Search .......................... 435/6, 91.1, 91.2; 536/23.1, 23.5, 24.3, 24.33

(56) References Cited

U.S. PATENT DOCUMENTS

| | | | | |
|---|---|---|---|---|
| 5,762,876 A | * | 6/1998 | Lincoln et al. | 422/67 |
| 6,183,955 B1 | * | 2/2001 | Andersson et al. | 435/6 |
| 2003/0225530 A1 | * | 12/2003 | Lowe et al. | 702/20 |

OTHER PUBLICATIONS

Waser et al. (Trends in Ecol. Evol. (1998) 13(2): 43–44).*
Keele et al. (J. Anim. Sci. (Jun. 1999) vol. 77 (6): 1364–1371).*
Stone et al. (J. Anim. Sci. (Jun. 1999) vol. 77(6): 1379–1384).*
Gallo et al. (Genetics (1997) 110: 1–12).*
Triggs (Science and Justice (2000) 40(1): 33–38).*
Ron et al. (J of Diary Science (1996) 79(4): 676–681).*
Hoeschele et al. (Genetics (1997) 147(3): 1445–1457).*
DeGroot, Morris H. et al., "Probability and Statistics" $3^{rd}$ ed. pp. 66–79 & 327.
Congiu et al., "The use of random amplified polymorphic DNA (RAPD) markers to identify strawberry varieties: a forensic application," *Molecular Ecology* 9:229–232, 2000.
Cornuet et al., "New Methods Employing Multilocus Genotypes to Select or Exclude Populations as Origins of Individuals," *Genetics* 153:1989–2000, 1999.
Ellegren et al., "DNA fingerprinting in horses using a simple (TG)n probe and its application to population comparisons," *Anim Genet* 23:1–9, 1992.
Gwakisa et al., "Characterization of Zebu cattle breeds in Tanzania using random amplified polymorphic DNA markers," *Anim Genet* 25:89–94, 1994.
Kantanen et al., "Random amplified polymorphic DNA in cattle and sheep: application for detecting genetic variation," *Anim Genet* 26(5):315–20, 1995.
Luikart et al., "Power of 22 micorsatellite markers in fluorescent multiplexes for parentage testing in goats (*Capra hircus*)," *Anim Genetics* 30:431–438, 1999.
MacHugh et al., "Genetic structure of seven European cattle breeds assessed using 20 microsatellite markers," *Anim Genetics* 29:333–340, 1998.
Ovilo et al., "Characterisation of Iberian pig genotypes using AFLP markers," *Anim Genetics* 31:117–122, 2000.
Paetkau et al., "Microsatellite analysis of population structure in Canadian polar bears," *Mol Ecol*—4:347–54, 1995.
Paszek et al., "Livestock Variation of Linked Microsatellite Markers in Diverse Swine Breeds," *Animal Biotechnology* 9:55–66, 1998.
Peelman et al., "Evaluation of the genetic variability of 23 bovine microsatellite markers in four Belgian cattle breeds," *Animal Genetics*, 29, 161–167, 1998.
Rannala and Mountain, "Detecting immigration by using multilocus genotypes," *Proc. Natl. Acad. Sci. USA* 94:9197–9201, 1997.
Rincon et al., "Genomic polymorphism in Uruguyayan Creole cattle using RAPD and microsatellite markers," *Res Vet Sci* 69:171–174, 2000.
Weir, B.S., Genetic Data Analysis II, Chapter 3, 71–114, Sinauer Associates, Inc., Sunderland, MA, 1996.

* cited by examiner

*Primary Examiner*—Carla J. Myers
*Assistant Examiner*—Alexander H. Spiegler
(74) *Attorney, Agent, or Firm*—Morrison & Foerster LLP

(57) ABSTRACT

This invention provides methods of assigning an individual to a population of origin based on statistical analyses of the individual's genotype and the genetic architecture of the underlying populations from which the individual may have originated.

22 Claims, No Drawings

METHOD FOR ASSIGNING AN INDIVIDUAL TO A POPULATION OF ORIGIN BASED ON MULTI-LOCUS GENOTYPES

BACKGROUND OF THE INVENTION

Throughout this application, various publications are referenced in parentheses by author and year. Full citations for these references may be found at the end of the specification immediately preceding the claims. The disclosures of these publications in their entireties are hereby incorporated by reference into this application to more fully describe the state of the art to which this invention pertains.

The assignment of an individual to a population of origin based upon the individual's multi-locus genotype is a statistical problem which must consider features of the genetic architecture of the underlying populations from which the individual may have originated. For example, if there exist population specific alleles at certain loci (the frequency of a population specific allele is zero in all but one of the populations), then the presence of at least one of these alleles in the genotype of an individual indicates unequivocally the population to which the individual belongs. Unfortunately, it is often difficult to establish that certain alleles are population specific, since their absence in a sample of individuals from any one population may be either because the alleles are truly population specific, or because the frequencies of these alleles are low and the sample obtained from any given population was small. Clearly, the absence of an allele in a sample from a population does not justify the assumption that the allele is not present in the population.

In the absence of a definitive marker for population of origin, or in the case where a genotype potentially exists in more than one population, statistical approaches must be employed to identify the most likely population of origin from among a set of "candidate populations." Further, these approaches must also evaluate the strength of evidence for the individual belonging to the most likely population of origin over the other competing candidate populations. Finally, the strength of evidence supporting the individual belonging to the most likely population of origin against another novel population that is not represented among the set of candidate populations must also be evaluated.

The present application discloses a statistical model for the assignment of individuals to a population of origin that possesses the following features:

1. The approach assumes that samples of individuals are available from a number of candidate populations and that these individuals have been genotyped for a number of marker loci.

2. There may be any number of candidate populations and each population may have a different sample size.

3. There may be any number of markers that have been genotyped in the individuals within each of the candidate populations.

4. The individual to be assigned to a population of origin may have been genotyped for all, or only a subset of the marker loci.

5. Marker loci genotypes in each candidate population are tested for conformance to Hardy-Weinberg Equilibrium (HWE) and Gametic Phase Equilibrium (GPE) expectations.

6. Under the null hypothesis that an individual belongs to any one given candidate population, the probability of the multi-locus genotype is computed for that population.

7. The posterior probability of the individual belonging to each of the candidate populations is then calculated utilizing any available prior knowledge concerning the population of origin.

8. The most likely population of origin of the tested individual is that population which possesses the greatest posterior probability of origin. It is recommended that an individual be assigned to that population only when the posterior probability of origin exceeds a threshold, such as 80%.

9. The percentage of genotypes more rare than the genotype of the individual in the most likely population of origin can be calculated or simulated in order to ascertain whether the individual may actually belong to a novel population not included in the set of candidate populations.

This model has application for example in the livestock industry for assigning an individual animal to a breed or to a population based on a desirable trait such as animal growth, quality grade, yield grade, marbling, rib-eye muscle area, dressing percentage, or meat tenderness.

SUMMARY OF THE INVENTION

The present invention provides a method of assigning an individual to a population of origin, which comprises:

(a) identifying a set of candidate populations of origin, wherein each candidate population is characterized by genotype frequencies and allele frequencies at one or more marker loci;

(b) determining a population prior genotype probability for each individual and candidate population of origin using knowledge concerning the individual which is available prior to genotyping the individual;

(c) genotyping the individual to identify the alleles at one or more of the marker loci identified in step (a) to thereby identify the individual's genotype;

(d) based on the identified genotype of the individual, sequentially determining a population genotype probability for each candidate population of origin under a null hypothesis that the individual arose from the population;

(e) combining the population prior genotype probability from step (b) and the population genotype probability from step (d) to obtain a population posterior genotype probability for each candidate population of origin;

(f) identifying a most likely population of origin wherein the population has the largest posterior genotype probability among the set of candidate populations; and (g) assigning the individual to the population identified in step (f).

DETAILED DESCRIPTION OF THE INVENTION

The following definitions are presented as an aid in understanding this invention.

As used herein a marker locus is defined as a unique location on a chromosome (locus) within the nuclear genome of an individual, at which variation among chromosomes and individuals may be detected. Examples include but are not limited to microsatellite, Restriction Fragment Length Polymorphism (RFLP), Random Amplified Polymorphic DNA (RAPD), Variable Number of Tandem Repeat (VNTR), and Single Nucleotide Polymorphism (SNP) loci. Marker loci are usually named, and the name expressed in italics. For example, AGLA17 is a microsatellite locus located at the centromeric end of chromosome 1 in cattle.

An allele is a genetic variant at a marker locus detected on a single chromosome. For example, for the A locus there may be n possible alleles and each allele is individually designated as $A_1, A_2, \ldots, A_n$.

The allele frequency is the frequency of an allele $A_i$ at the A locus within a specific population and is defined as $F(A_i)=P_{Ai}$ such that $$\sum_{i=1}^{n} p_{Ai} = 1.$$

Diploid means the nuclear genome of the individual possesses pairs of chromosomes, in which one chromosome of each pair is transmitted by each parent. Without loss of generality, the methodology described here will be for diploid species.

Genotype is defined as the combination of alleles at a single locus that is found within an individual. Genotypes at the A locus are of the form $A_iA_j$ for i and j between 1 and n. Individuals possessing two identical alleles $A_iA_i$ are called homozygotes and individuals possessing two different alleles ($i \neq j$) heterozygotes. Similarly a multi-locus genotype is represented as the genotypes at each locus, e.g., $A_1A_2B_3B_3C_4C_5$.

Genotyping an individual means to analyze a sample of deoxyribonucleic acid (DNA) from the individual to identify the alleles present at one or more marker loci.

A haplotype is defined to be the set of alleles at multiple loci that are present in a gamete (sperm or ova). If there are $n_a$, $n_b$ and $n_c$ alleles present at the A, B and C loci, haplotypes are represented as $A_iB_jC_k$ for $i=1, \ldots, n_a$; $j=1, \ldots, n_b$ and $k=1, \ldots, n_c$.

Hardy-Weinberg Equilibrium (EWE) means that in a random mating population in which there is no selection, migration, mutation or drift, population genotype frequencies occur as a simple function of allele frequencies. Among homozygotes $F(A_iA_i)=p_{Ai}^2$ and among heterozygotes $F(A_iA_j)=2p_{Ai}p_{Aj}$.

Gametic Phase Equilibrium (GPE): Two (or more) loci are defined as being in GPE if all population haplotype frequencies occur as the product of individual allele frequencies, viz. $F(A_iB_jC_k)=p_{Ai}p_{Bj}p_{ck}$ for $i=1, \ldots, n_a$; $j=1, \ldots, n_b$ and $k=1, \ldots, n_c$. For loci that are in GPE, individual loci are in HWE, and multi-locus genotype frequencies are obtained as the product of individual locus genotype frequencies. For example, $F(A_1A_2B_3B_3C_4C_5)=F(A_1A_2)F(B_3B_3)F(C_4C_5)= (2p_{A1}p_{A2})(p_{B3}^2)(2p_{c4}p_{c5})=4p^{A1}p_{A2}p_{B3}^2p_{c4}p_{c5}$.

A candidate population is a population from which a sample of individuals has been genotyped for multiple marker loci and sample allele frequencies have been determined for each locus.

Having due regard to the preceding definitions, the present invention concerns a method of assigning an individual to a population of origin, which comprises:

(a) identifying a set of candidate populations of origin, wherein each candidate population is characterized by genotype frequencies and allele frequencies at one or more marker loci;

(b) determining a population prior genotype probability for each individual and candidate population of origin using knowledge concerning the individual which is available prior to genotyping the individual;

(c) genotyping the individual to identify the alleles at one or more of the marker loci identified in step (a) to thereby identify the individual's genotype;

(d) based on the identified genotype of the individual, sequentially determining a population genotype probability for each candidate population of origin under a null hypothesis that the individual arose from the population;

(e) combining the population prior genotype probability from step (b) and the population genotype probability from step (d) to obtain a population posterior genotype probability for each candidate population of origin;

(f) identifying a most likely population of origin wherein the population has the largest posterior genotype probability among the set of candidate populations; and (g) assigning the individual to the population identified in step (f).

In one embodiment of the method, the individual is only assigned to the most likely population of origin if the posterior genotype probability for the most likely population of origin exceeds a threshold value. In one embodiment, the threshold value is determined empirically. In one embodiment, the threshold value is determined using a sample of individuals from each candidate population who are independent of individuals used to characterize each candidate population. In one embodiment, the threshold value is varied to determine the percentage of individuals who a) cannot be classified to a population of origin, b) are correctly classified, and c) are incorrectly classified.

In one embodiment, the method further comprises:

(a) computing a probability with which genotypes rarer than the individual's genotype occur in the most likely population of origin; and (b) if the probability in step (a) is above a threshold value, assigning the individual to the population of origin previously identified as the most likely population of origin, or if the probability in step (a) is not above a threshold value, assigning the individual to a novel population that is not represented among the set of candidate populations of origin.

In one embodiment, the threshold value is determined empirically. In one embodiment, the threshold value is determined using a sample of individuals from each candidate population who are independent of individuals used to characterize each candidate population. In one embodiment, the threshold value is varied to reduce the percentage of individuals who are incorrectly classified to a population.

In one embodiment of the method, the population prior genotype probability is based on one or more morphological features of the individual. In a further embodiment, one or more morphological features allow the exclusion of one or more candidate populations of origin. In different embodiments, one or more morphological features are selected from the group consisting of coat color, presence or absence of horns, and presence or absence of Bos indicus (humped or Zebu cattle) features such as a shoulder hump or a long, downswept ear. In a further embodiment, the coat color is black or nonblack.

In one embodiment, the population prior genotype probability is set to equal a proportion of total population size that comprises each candidate population of origin. In another embodiment, the population prior genotype probability is assumed to be uniform for each candidate population of origin.

In one embodiment of the method, the marker locus genotypes for each candidate population of origin are in Hardy-Weinberg Equilibrium and Gametic Phase Equilibrium. In other embodiments, the marker locus genotypes for each candidate population of origin are not in Hardy-Weinberg Equilibrium or Gametic Phase Equilibrium.

In one embodiment of the method, the individual is an animal. In further embodiments, the animal is a cow, a heifer, a steer, a bull, a bullock, a pig, a horse, a fish, a chicken, a duck, a lamb, a shrimp, an oyster, a mussel, or a shellfish.

In one embodiment of the method, the candidate population of origin is selected based on a desirable trait. In further embodiments, the desirable trait is selected from the group consisting of one or more of animal growth, quality grade, yield grade, marbling, rib-eye muscle area, dressing percentage, meat tenderness, meat flavor, meat palatability, fatness, fat color, unsaturated fatty acid content of fat, reproductive efficiency, prolificacy, disease resistance, feed conversion efficiency, drought tolerance, and heat tolerance. Marbling score in beef cattle is a subjective score assigned by a United States Department of Agriculture (USDA) grader to a carcass based upon the amount of intramuscular fat visualized in the longissimus dorsi muscle at the 12th to 13th rib juncture in properly chilled carcasses (United States Standards for Grades of Carcass Beef, 1997). Ribeye muscle area is the cross-sectional area of the longissimus dorsi muscle at the 11th to 12th rib juncture and is measured subjectively or by means of a grid calibrated in tenths of an inch at the same time as the marbling score is obtained. Quality grade is assigned by the USDA grader and is a combination of the marbling score and maturity (age) of the animal estimated from the size, shape and ossification of the bones and cartilages (especially the split chine bones) and the color and texture of the flesh. Younger animals (A maturity) are not penalized, but older animals (B maturity) have their marbling scores down rated into the quality grade. Yield grade is assigned by the USDA grader and is an estimate of the yield of closely trimmed (½ inch fat or less), boneless retail cuts expected to be derived from the major wholesale cuts (round, sirloin, short loin, rib, and square-cut chuck) of a carcass. The yield grade of a beef carcass is determined by considering four characteristics: the amount of external fat; the amount of kidney, pelvic and heart fat; the area of ribeye muscle; and the carcass weight. Carcasses possessing large amounts of exterior and interior fat receive larger yield grade scores indicating lower yields of lean meat. Dressing percentage is the ratio of hot carcass weight (the eviscerated carcass) to live animal weight immediately preslaughter and expressed as a percentage.

In one embodiment of the method, the candidate population of origin is selected based on an undesirable trait. In a further embodiment, the undesirable trait is toughness of meat.

This invention will be better understood from the methodology and examples which follow. However, one skilled in the art will readily appreciate that the specific methods and examples discussed are merely illustrative of the invention as described more fully in the claims which follow thereafter.

Methodology

Candidate Population Data

Baseline data are gathered for each of the populations that are going to be candidates for the assignment of individuals. This should represent all of the known extant populations. The process involves sampling individuals from each population and genotyping them for the marker loci that are to be used in the classification process. The larger the number of individuals in each sample the better; 50 individuals is a "reasonable" target. Fewer individuals will sometimes be necessary for small populations.

The data that are collected on the individuals to characterize the candidate populations are used to: a) estimate allele frequencies in the candidate population, b) estimate genotype frequencies in the candidate population, and c) test to determine if the marker loci are in Hardy-Weinberg Equilibrium and Gametic Phase Equilibrium in each of the candidate populations. The allele frequencies are estimated by counting the number of alleles of each type that are present in the sample and expressing the totals as a proportion of the total number of alleles in the sample. Similarly, the genotype frequencies for each marker locus are estimated by counting the number of genotypes of each type that are present in the sample and expressing the totals as a proportion of the total number of genotypes in the sample.

The numbers of alleles present in the sample from each population are tabulated. Let $N^1$ be the number of alleles present in the sample of individuals which are known with certainty as having originated from the $i^{th}$ candidate population $i=1, \ldots, p$. In a diploid species, $N^i$ is twice the number of individuals in the sample and the sample size may vary among the p populations. Suppose that a series of m marker loci are genotyped in all individuals and populations. Within each population, the resulting genotype counts may be tested for Hardy-Weinberg Equilibrium (HWE) and Gametic Phase Equilibrium (GPE) using the well known likelihood ratio or $x^2$ "goodness of fit" tests, as described for example in Weir (1996). Without loss of generality, we assume that each of the candidate populations is found to be in HWE and GPE. Further, the number of alleles present in the sample for each marker locus and each population is tabulated as follows. Let $n_{Aj}{}^i$ be the number of $A_j$ alleles detected in the sample from the $i^{th}$ population. The data for locus A (and similarly for the remaining marker loci) may be represented as:

| | A locus alleles | | | | |
|---|---|---|---|---|---|
| Population | $A_1$ | $A_2$ | ... | $A_{na}$ | 93 |
| 1 | $n_{A1}{}^1$ | $n_{A2}{}^1$ | ... | $n_{Ana}{}^1$ | $N^1$ |
| 2 | $n_{A1}{}^2$ | $n_{A2}{}^2$ | ... | $n_{Ana}{}^2$ | $N^2$ |
| . | . | . | . | . | |
| . | . | . | . | . | |
| . | . | . | . | . | |
| p | $n_{A1}{}^p$ | $n_{A2}{}^p$ | ... | $n_{Ana}{}^p$ | $N^p$ |

Note that certain of the $n_{Aj}{}^i=0$ if the $j^{th}$ allele at the A locus is not detected in the same from the $i^{th}$ population.

As an example, suppose that at the A locus we observes three alleles $A_1$, $A_2$ and $A_3$. The individuals are diploid, so genotype is defined by the combination of two alleles that are present in any one individual. Assume that when we genotype 120 individuals from a given candidate population, we observe the following:

| Genotype | Number of individuals |
|---|---|
| $A_1A_1$ | 22 |
| $A_1A_2$ | 12 |
| $A_1A_3$ | 8 |
| $A_2A_2$ | 40 |
| $A_2A_3$ | 16 |
| $A_3A_3$ | 22 |
| Total | 120 |

The genotype frequencies are obtained from the sample as the relative frequencies of the genotypes, so for the $A_1A_1$ genotype we have a genotype frequency of 22/120=0.1833. To obtain the allele frequencies, we count the number of alleles present in the sample using the genotype counts above. So there are 22 $A_{1A1}$ individuals with 2 $A_1$ alleles, 12 $A_1A_2$ individuals with 1 $A_1$ allele and 8 $A_{1A3}$ individuals with 1 $A_1$ allele. This gives us a total of 64 $A_1$ alleles.

Therefore:

| Allele | Number of alleles |
|---|---|
| $A_1$ | 64 |
| $A_2$ | 108 |
| $A_3$ | 68 |
| Total | 240 |

The total number of alleles is of course twice the total number of individuals.

Candidate Population Prior Genotype Probabilities

For each individual to be tested, prior probabilities are assigned for the probability of belonging to each of the candidate populations. Prior probabilities are assigned based on knowledge that is available before the DNA sample from an individual was analyzed for marker genotype information. If there is no prior information then each population is assigned an equal prior probability of having given rise to the individual. Alternatively, certain morphological data may be available on an individual which allow the exclusion of certain of the candidate populations, in which case the prior probabilities of these populations for this individual are set to zero. If, for example, the individual is a horned animal and only three out of ten candidate populations contain horned animals, the prior probabilities for the seven non-horned populations would be set to zero and the prior probabilities for the three horned populations would each be set to ⅓ in the absence of further information.

Let $P_{ij}$ represent the a priori or prior probability that the $j^{th}$ individual originated from the $i^{th}$ population. If individuals are sampled at random with respect to population of origin, we should elect to set the population prior probabilities equal to the proportion of the total population size that comprises each candidate population. If no pre-existing information was available, we assume a non-informative or uniform prior of $P_{ij}=1/p$ for $i=1, \ldots, p$. Hence the individual had an equal chance of originating from any of the p candidate populations when a uniform prior is used.

Prior probabilities may differ for each individual that is to be tested, but in every case must sum to unity as $$\sum_{i=1}^{p} P_{ij} = 1.$$

Candidate Population Genotype Probabilities

Each individual is genotyped for the marker loci for which baseline information was gathered for each candidate population. The individual's genotype probability is then estimated (using a maximum likelihood approach) for each of the candidate populations.

Suppose that an individual that is to be assigned to a population is genotyped for the m marker loci and, arbitrarily, the multi-locus genotype is determined to be $A_1A_2B_3B_3 \ldots M_4M_5$. The probability of this genotype occurring in the $i^{th}$ population is determined as follows:

1. Under the null hypothesis that the individual originated from the $i^{th}$ population, the individual may be incorporated into the sample data for this population and the allele counts at each locus updated. For example, at the A locus, the sample counts for the $i^{th}$ population become:

| Allele | $A_1$ | $A_2$ | $A_3$ | ... | $A_{na}$ | $\Sigma$ |
|---|---|---|---|---|---|---|
| Allele Count | $n_{A1}^i + 1$ | $n_{A2}^i + 1$ | $n_{A3}^i$ | ... | $n_{Ana}^i$ | $N^i + 2$ |

Similarly, at the B locus, the sample counts for the $i^{th}$ population become:

| Allele | $B_1$ | $B_2$ | $B_3$ | ... | $B_{na}$ | $\Sigma$ |
|---|---|---|---|---|---|---|
| Allele Count | $n_{B1}^i$ | $n_{B2}^i$ | $n_{B3}^i + 2$ | ... | $n_{Bnb}^i$ | $N^i + 2$ |

2. Under the assumption of Hardy-Weinberg Equilibrium in the $i^{th}$ population, the maximum likelihood estimate (MLE) of genotype frequency at each of the marker loci is obtained. For example, at the A locus, the MLE of the probability of the $A_1A_2$ genotype $F_i(A_1A_2)$ is $2(n_{A1}^i+1)(n_{A2}^i+1)/(N^i+2)^2$. At the B locus, the MLE of the probability of the $B_{3B3}$ genotype $F_i(B_3B_3)$ is $(n_{B3}^i+2)^2/(N^i+2)$ 3. Under the assumption of Gametic Phase Equilibrium in the $i^{th}$ population, the MLE of the multi-locus genotype frequency is obtained as the product of the genotype frequencies at each of the marker loci. Thus, the MLE of the probability of the $A^1A_2B_3B_3 \ldots M_4M_5$ genotype in the $i^{th}$ population $F_i(A_1A_2B_3B_3 \ldots M_4M_5)$ is: $\{2(n_{A1}+1)(n_{A2}^i+1)/(N^i+2)^2\}\{(n_{B3}^i+2)^2/(N^i+2)^2\} \ldots \{2(n_{M4}^i+1)(n_{M5}^i+1)/(N^i+2)^2\}$.

In general, let $G_j$ represent the multi-locus genotype of the $j^{th}$ individual. Then $F_i(G_j)$ represents the probability of the genotype of the $j^{th}$ individual in the $i^{th}$ population.

If the candidate population is not in Hardy-Weinberg and Gametic Phase Equilibrium, the population genotype frequency is estimated by the frequency of the individual's genotype in the sample from each candidate population. This process involves sequentially adding the individual to the sample so that the frequency of any genotype that was not present in the original sample is $1/(N+1)$ where N is the number of individuals sampled for the population.

Candidate Population Posterior Genotype Probabilities

The posterior probabilities that the individual belongs to each of the candidate populations are determined, and the population with the largest probability is selected as the "most likely" population of origin.

The posterior probability of the $j^{th}$ individual's genotype originating from the $i^{th}$ candidate population is obtained by combining both the population prior genotype probabilities and the candidate population genotype probabilities as follows:

$$\Phi_{ij} = \frac{P_{ij}F_i(G_j)}{\sum_{l=1}^{p} P_{lj}F_l(G_j)}.$$

For the $j^{th}$ individual, $\Phi_{ij}$ is computed for each population $i=1, \ldots, p$ and the population with the greatest $\Phi_{ij}$ value is the most likely population of origin among the set of candidate populations.

Simply taking the population with the largest posterior probability as being the "most-likely" population of origin may not be a very good decision rule. The additional steps to the procedure described below are designed to help the user arrive at a decision rule that has quantified success and error rates.

A threshold value must be determined for the posterior probability in order to define a decision rule for accepting an individual as originating in one of the candidate populations. For example, one may choose to accept an individual as originating in a population if $\Phi_{ij}$ exceeds 0.90 for one population. This is interpreted to mean that among the available candidate populations, there is a 90% chance the individual originated from the most likely population and only a 10% chance of originating in any of the other populations. Individuals that are hybrids typically produce approximately equal posterior probabilities of belonging to the two populations that contributed the parents of the hybrid and thus these hybrid animals are generally not assigned to any one population.

If a second set of samples of individuals from each of the populations is available or can be obtained that are independent of the samples used to produce the baseline candidate population data, these individuals can be genotyped and posterior probabilities can be calculated for each individual and each of the candidate populations. A decision rule can then be empirically determined that meets the requirements of the user. For example, the user may wish to ensure that 95% of the individuals that are assigned to a population are correctly assigned. Thus, one may find that assigning an individual to a population only when the posterior probability of belonging to that population is greater than 90% results in 95% of individuals being correctly assigned to their population of origin. By altering the threshold for the posterior probability decision rule, one can determine the proportion of individuals that are correctly classified, incorrectly classified and not classified respectively. Individuals for which the largest posterior probability falls below the threshold are not assigned to a population.

Rarity of Genotype in Candidate Population

Occasionally an individual may be incorrectly assigned to a population because the individual arose from a population that was not represented in the group of candidate populations. In this case, the procedure described above will identify the population that is most similar to the population from which the individual actually arose. If the posterior probability is greater than the threshold (i.e., all of the remaining populations are quite different to the population from which the individual actually arose), the individual will be incorrectly assigned. These cases of incorrect assignment can be identified by calculating the probability of a rarer genotype in the assigned population. If this probability is low, say 5% (this threshold is also user defined and can also be determined empirically), then one might reject the individual from the population and change the classification of the individual to "unassigned." The underlying logic here is that even though the individual shows strong evidence for belonging to only one of the populations, it is actually a rare genotype in that population. From a statistical perspective, it is more likely that the individual actually has a fairly common genotype in a population that is not represented among the candidate populations.

If there are m marker loci and there are nk alleles at the $k^{th}$ marker, there will be $$T = \prod_{k=1}^{m} \frac{n_k(n_k+1)}{2}$$

possible multi-locus genotypes in any population. It does not require many loci or many alleles at the individual marker loci for the total number of genotypes, T, to become very large. For example, with m=10 marker loci and $n_k$=6 alleles at each locus (which is characteristic of microsatellite loci), there are more than a trillion possible genotypes. In this case, we estimate the frequency of a genotype that is rarer than the genotype present in the tested individual by simulation. A large number of multi-locus genotypes (such as 100,000) is simulated by drawing alleles at random from the most likely population using the relative allele frequencies for the population after adding the alleles of the individual to the sample. The probability of each of the simulated genotypes is then computed as described above. Finally, the percentage of simulated genotypes for which the multi-locus genotype frequency is lower than that of the tested individual is calculated. If the percentage of rarer genotypes is low, say 5% or less, we might conclude that the tested individual has a genotype that is too rare for it to truly have originated in the most likely population and that the individual actually belongs to a novel population.

Advantageous Features of the Approach

The approach described herein provides certain advantages including, but not limited to, the following:

1. The approach assumes that any allele that is present in an individual to be tested but that is absent from the sample for any one candidate population, is absent because it is a rare allele that was not captured in the sample rather than the allele being population specific. This approach loses statistical power in the sense that population specific alleles unequivocally eliminate from consideration any candidate population that does not possess the alleles. However, central to this argument is the fact that without very large samples of individuals from each of the candidate populations, it is impossible to discriminate between alleles that are rare and alleles that are absent from any population. Thus, the approach presented herein is conservative in that it will underestimate the posterior probability of population of origin when there are population specific alleles. On the other hand, our approach gains specificity in that populations are not rejected from consideration simply because an allele was not present in the sample of individuals drawn from the population.

2. The approach recognizes that there may well be a number of potential populations that were not selected as candidates because they were not sampled in order to define them as a candidate population. There may well be individuals that are submitted for testing that originated in some novel and unsampled population. These individuals will have posterior probabilities of population of origin estimated by the procedure and will be assigned to the candidate population that is genetically most similar to the true population of origin. In some cases, the posterior probability for one candidate population may be very high, even though the individual did not originate from this population. In order to identify misclassifications, we estimate the cumulative probability distribution function for genotypes that are rarer than that of the individual to be classified. This allows estimation of the probability of a rarer genotype in the most likely population of origin of the individual. If this probability is low, perhaps 5% or less, one should conclude that the individual actually originated in a population not included in the candidate set, since only 5% of genotypes are rarer in the most likely of the candidate populations.

3. The power of the approach depends on the number of marker loci that are typed in the individuals to be classified and the candidate populations and the degree to which marker allele frequencies are skewed among the candidate populations. However, the approach is able to utilize all available information. If certain individuals have been genotyped for only a subset of the available markers, the candidate population genotype probabilities and therefore the posterior probabilities are computed only for the available multi-locus marker genotype.

4. The probability thresholds for assigning an individual to a population of origin based upon the posterior probability and for accepting the individual as truly belonging to the most likely is population based upon the probability of a rarer genotype must be determined empirically. Preferably a second independent sample from each of the candidate populations should be genotyped and posterior probabilities computed for each candidate population. By varying an artificial posterior probability threshold for accepting an individual as belonging to the most likely population of origin, we can empirically determine the percentage of individuals that a) cannot be classified to a population of origin, b) are correctly classified, and c) are incorrectly classified. Among those individuals that are incorrectly classified to a population based upon the posterior probability, altering the acceptance threshold for the percentage of rarer genotypes further allows the reduction in the overall percentage of misclassified individuals.

EXAMPLE

Consider the following three candidate populations, which have been genotyped for two marker loci. The A locus has 2 alleles and the B locus 3 alleles if we ignore the subdivision into candidate populations. The individuals that were genotyped for the two loci from each of the candidate populations gave the following allele counts:

|            | A locus alleles |       |    |
|------------|-----------------|-------|----|
| Population | $A_1$           | $A_2$ | Σ  |
| 1          | 20              | 20    | 40 |
| 2          | 20              | 30    | 50 |
| 3          | 50              | 10    | 60 |

|            | B locus alleles |       |       |    |
|------------|-----------------|-------|-------|----|
| Population | $B_1$           | $B_2$ | $B_3$ | Σ  |
| 1          | 10              | 20    | 10    | 40 |
| 2          | 50              | 0     | 0     | 50 |
| 3          | 0               | 5     | 55    | 60 |

Suppose that the first individual presented for classification to a population of origin has genotype $G_1 = A_1A_1B_3B_3$. The candidate population genotype probabilities are:

$$F_1(G_1) = \{22^2/42^2\}\{12^2/42^2\} = 0.0224,$$

$$F_2(G_1) = \{22^2/52^2\}\{2^2/52^2\} = 0.0003,$$

$$F_3(G_1) = \{52^2/62^2\}\{57^2/62^2\} = 0.5946.$$

We shall assume that this individual has an equal a priori chance of originating from any of the three populations and hence $P_{11} = P_{21} = P_{31} = \frac{1}{3}$.

The posterior probabilities of belonging to each of the candidate populations are:

$$\Phi_{11} = \frac{0.33 \times 0.0224}{0.33 \times 0.0224 + 0.33 \times 0.0003 + 0.33 \times 0.5946} = .0363$$

$$\Phi_{21} = \frac{0.33 \times 0.0003}{0.33 \times 0.0224 + 0.33 \times 0.0003 + 0.33 \times 0.5946} = .0004$$

$$\Phi_{31} = \frac{0.33 \times 0.5946}{0.33 \times 0.0224 + 0.33 \times 0.0003 + 0.33 \times 0.5946} = .9633$$

Since the magnitude of the posterior probability for the third population exceeds a threshold (which we shall arbitrarily set at 0.90 for the purposes of this example), we can conclude at this stage that the individual originated either from the third candidate population or from a novel population genetically similar to the third candidate population. In order to discriminate between these two situations, we must compute the probability of a rarer genotype than $A_1A_1B_3B_3$ in the third candidate population. Since there are only 18 possible genotypes for this example, we do not need to simulate the distribution of genotypes and provide the distribution;

| Genotype       | Population 3 Frequency |
|----------------|------------------------|
| $A_1A_1B_1B_1$ | 0.0000                 |
| $A_1A_1B_1B_2$ | 0.0000                 |
| $A_1A_1B_1B_3$ | 0.0000                 |
| $A_1A_1B_2B_2$ | 0.0046                 |
| $A_1A_1B_2B_3$ | 0.1043                 |
| $A_1A_1B_3B_3$ | 0.5946                 |
| $A_1A_2B_1B_1$ | 0.0000                 |
| $A_1A_2B_1B_2$ | 0.0000                 |
| $A_1A_2B_1B_3$ | 0.0000                 |
| $A_1A_2B_2B_2$ | 0.0018                 |
| $A_1A_2B_2B_3$ | 0.0401                 |
| $A_1A_2B_3B_3$ | 0.2287                 |
| $A_2A_2B_1B_1$ | 0.0000                 |
| $A_2A_2B_1B_2$ | 0.0000                 |
| $A_2A_2B_1B_3$ | 0.0000                 |
| $A_2A_2B_2B_2$ | 0.0002                 |
| $A_2A_2B_2B_3$ | 0.0039                 |
| $A_2A_2B_3B_3$ | 0.0220                 |
| Σ              | 1.0000.                |

The genotype distribution reveals that the $A_1A_1B_3B_3$ genotype is the most common genotype in the third candidate population and that fully 40.54% of individuals within this population have genotypes that are more rare than the genotype of the tested individual. Therefore we conclude that the tested individual originated from the third candidate population and not from a novel population that was similar in genetic structure.

Applications

The approach disclosed herein has application for example in the livestock industry where there is a need to be able to determine value differences in live animals due to the inherent genetic variation in the yield of tender and marbled beef from their carcasses. Packers are forced to sort through thousands of carcasses from animals slaughtered each day in order to identify those that meet the specifications of their customers. Due to the very high daily volume of slaughter animals and limited cooler space (which reduces ability to sort), packers are unable to efficiently market their inventory based upon quality specifications. Further, packers have no ability to discriminate among the carcasses that do not grade choice that could be marketed as a tender product. By and large, the variation in product specifications that the packers must manage each day correlates directly to the variation in the cattle received.

Knowledge of an animal's underlying genetic predisposition to yield marbled and tender beef would allow the stratification of the existing commodity market to facilitate the management and marketing of animals based upon product specifications. As much as 50 percent of the variation in growth and carcass yield and quality attributes in cattle is determined by the additive effects of genes. The remaining variation is due to the environment that an animal is exposed to prior to entry to the feedlot and due to the management the animal receives during the feedlot and slaughter phases of production. Thus, at least 50 percent of the variation that currently exists within the commodity cattle market could be eliminated by grouping cattle according to their individual genotypes at entry into the feedlot. These animals could then be managed, fed and slaughtered as a uniform group and could then be marketed according to their quality attributes. This model would allow the creation of new "branded" products for the marketing of products such as lean and tender beef.

The approach described in the present application can be applied not only to beef cattle but also to other livestock such as fish, pigs, chickens, lambs, shrimp, mussels, oysters, and shellfish.

References

United States Standards for Grades of Carcass Beef, United States Department of Agriculture, Agricultural Marketing Service, Livestock and Seed Division. Washington, D.C., pages 1–17, 1997 [available at http://meat.tamu.edu/pdf/beef-car.pdf].

Weir, B. S. Genetic Data Analysis II. Sinauer Associates, Inc., Sunderland, Mass., 1996.

What is claimed is:

1. A method of assigning a non-human individual to a population of origin, which comprises:
    (a) identifying a set of candidate populations of origin, wherein each candidate population is characterized by genotype frequencies and allele frequencies at one or more marker loci;
    (b) assigning a population prior genotype probability for an individual and said each candidate population using knowledge concerning the individual which is available prior to genotyping the individual;
    (c) genotyping the individual to identify alleles at the one or more marker loci in step (a) to thereby identify the individual's genotype;
    (d) sequentially calculating a population genotype probability for the individual and said each candidate population based on the genotype of the individual under a null hypothesis that the individual arose from said each candidate population;
    (e) combining the population prior genotype probability from step (b) and the population genotype probability from step (d) to calculate a population posterior genotype probability for the individual and said each candidate population;
    (f) identifying a most likely population of origin, wherein the most likely population of origin has the largest population posterior genotype probability among the set of candidate populations; and
    (g) assigning the non-human individual to the most likely population of origin identified in step (f).

2. The method of claim 1, wherein the individual is only assigned to the most likely population of origin if the population posterior genotype probability for the most likely population of origin exceeds a threshold value.

3. The method of claim 1, which further comprises:
    (a) computing an additional probability with which genotypes rarer than the individual's genotype occur in the most likely population of origin; and
    (b) if the additional probability in step (a) is above a threshold value, assigning the individual to the most likely population of origin, or if the additional probability in step (a) is not above the threshold value, assigning the individual to a novel population that is not represented among the set of candidate populations of origin.

4. The method of claim 2, wherein the threshold value is determined empirically.

5. The method of claim 4, wherein the threshold value is determined using population posterior genotype probabilities of a sample of individuals from said each candidate population who are independent of individuals used to characterize said each candidate population.

6. The method of claim 4, wherein the threshold value is varied to determine the percentage of a sample of individuals who a) cannot be classified, b) are correctly classified, and c) are incorrectly classified.

7. The method of claim 3, wherein the threshold value is determined empirically.

8. The method of claim 7, wherein the threshold value is determined using population posterior genotype probabilities of a sample of individuals from said each candidate population who are independent of individuals used to characterize said each candidate population.

9. The method of claim 7, wherein the threshold value is increased to reduce the percentage of a sample of individuals who are incorrectly classified to one of the candidate populations of origin.

10. The method of claim 1, wherein the population prior genotype probability is based on one or more morphological features of the individual.

11. The method of claim 10, wherein the one or more morphological features allow the exclusion of one or more of the candidate populations of origin.

12. The method of claim 11, wherein the one or more morphological features are selected from the group consisting of coat color, presence or absence of horns, presence or absence of a shoulder hump, and presence or absence of a long, downswept ear.

13. The method of claim 12, wherein the coat color is black or nonblack.

14. The method of claim 1, wherein the population prior genotype probability for the individual and said each candidate population is set to equal a proportion of total population size in said each candidate population.

15. The method of claim 1, wherein the population prior genotype probability for the individual and said each candidate population is uniform.

16. The method of claim 1, wherein marker locus genotypes for said each candidate population are in Hardy-Weinberg Equilibrium and Gametic Phase Equilibrium.

17. The method of claim 1, wherein marker locus genotypes for said each candidate population are not in Hardy-Weinberg Equilibrium or Gametic Phase Equilibrium.

18. The method of claim 1, wherein the animal is a cow, a heifer, a steer, a bull, a bullock, a pig, a horse, a fish, a chicken, a duck, a lamb, a shrimp, an oyster, a mussel, or a shellfish.

19. The method of claim 1, wherein the alleles at the one or more marker loci are selected based on additive effects of the alleles on a desirable trait such that said assigning is based on the desirable trait.

20. The method of claim 19, wherein the desirable trait is selected from the group consisting of one or more of animal growth, quality grade, yield grade, marbling, rib-eye muscle area, dressing percentage, meat tenderness, meat flavor, meat palatability, fatness, fat color, unsaturated fatty acid content of fat, reproductive efficiency, prolificacy, disease resistance, feed conversion efficiency, drought tolerance, and heat tolerance.

21. The method of claim 1, wherein the alleles at the one or more marker loci are selected based on additive effects of the alleles on an undesirable trait such that said assigning is based on the undesirable trait.

22. The method of claim 21, wherein the undesirable trait is toughness of meat.

* * * * *

UNITED STATES PATENT AND TRADEMARK OFFICE
CERTIFICATE OF CORRECTION

PATENT NO. : 6,770,437 B1
DATED : October 4, 2004
INVENTOR(S) : Taylor et al.

It is certified that error appears in the above-identified patent and that said Letters Patent is hereby corrected as shown below:

Column 2,
Line 63, "AGLA17" should read -- *AGLA17* --.

Column 3,
Line 32, "(EWE)" should read -- (HWE) --; Column 3, line 46, that portion of the formula reading "$4p^{A1}p_{A2}p_{B3}p_{c4}p_{c5}$" should read -- $4p_{A1}p_{A2}p_{B3}p_{c4}p_{c5}$ --.

Column 4,
Line 51, "Bos indicus" should read -- *Bos indicus* --.

Column 6,
Line 36, that portion of the table reading "93" should read -- Σ --.

Column 7,
Line 2, "22 $A_{1A1}$" should read -- 22 $A_1A_2$ --;
Line 3, "8 $A_{1A3}$" should read -- 8 $A_1A_3$ --.

Column 8,
Line 14, that portion of the table reading "$B_{na}$" should read -- $B_{nb}$ --;
Line 24, "$B_{3B3}$" should read -- $B_3B_3$ --;
Line 24, that portion of the formula, at the terminus of the line, reading "$/(N^i+2)$" should read -- $/(N^i+2)^2$. --;
Line 29, "$A^1A_2B_3B_3$" should read -- $A_1A_2B_3B_3$ --;
Line 30, that portion of the formula reading "$\{2(n_{A1}+1)$" should read -- $\{2(n_{A1}^i+1)$ --.

UNITED STATES PATENT AND TRADEMARK OFFICE
CERTIFICATE OF CORRECTION

PATENT NO. : 6,770,437 B1
DATED : October 4, 2004
INVENTOR(S) : Taylor et al.

It is certified that error appears in the above-identified patent and that said Letters Patent is hereby corrected as shown below:

Column 9,
Lines 60-65, the formula reading: " $T = \prod_{k=1}^{in} \frac{n_k(n_k+1)}{2}$ " should read -- $T = \prod_{k=1}^{m} \frac{n_k(n_k+1)}{2}$ --.

Signed and Sealed this

Third Day of May, 2005

JON W. DUDAS
*Director of the United States Patent and Trademark Office*